United States Patent [19]

Eckwall

[11] Patent Number: 5,165,405
[45] Date of Patent: Nov. 24, 1992

[54] APPARATUS FOR TISSUE STIMULATION
[75] Inventor: Christer Ekwall, Spanga, Sweden
[73] Assignee: Siemens Aktiengesellschaft, Munich, Fed. Rep. of Germany
[21] Appl. No.: 727,054
[22] Filed: Jul. 8, 1991
[30] Foreign Application Priority Data Jul. 6, 1990 [EP] European Pat. Off. ............ 90112955

[51] Int. Cl.$^5$ ............................................ A61N 1/362
[52] U.S. Cl. ............................................ 128/419 PG
[58] Field of Search .................... 128/419 PG, 419 PT

[56] References Cited

U.S. PATENT DOCUMENTS

| 4,537,201 | 8/1985 | Delle-Vedove et al. | 128/697 |
| 4,674,509 | 6/1987 | DeCote, Jr. | 128/419 PT |
| 4,708,142 | 11/1987 | DeCote, Jr. | 128/419 PT |
| 4,913,146 | 4/1990 | DeCote, Jr. | 128/419 PG |

FOREIGN PATENT DOCUMENTS

0017848 10/1980 European Pat. Off. .

Primary Examiner—William E. Kamm
Assistant Examiner—Scott M. Getzon
Attorney, Agent, or Firm—Hill, Van Santen, Steadman & Simpson

[57] ABSTRACT

In the stimulation of living tissue the reaction thereof is usually superimposed with polarization phenomena to such a degree that the reaction cannot be recognized in the electrical signal. To avoid this problem, a curve of the measured tissue potential is intermediately stored in a first memory after each stimulation, and the intermediately stored curve is then always used for updating the current signal curve. The current signal curve is stored in a second memory whenever an absence of a tissue reaction to the stimulation occurs.

11 Claims, 4 Drawing Sheets

APPARATUS FOR TISSUE STIMULATION

BACKGROUND OF THE INVENTION

1. Field of the Invention

The present invention is directed to an arrangement for tissue simulation, in particular a heart pacemaker, which includes a substraction stage for generating a different signal from measured cardiac electrical potential and a curve representing polarization phenomena produced in the tissue by stimulation, with the stimulation being controlled dependent on an evaluation of the difference signal.

2. Description of the Prior Art

A heart pacemaker disclosed in U.S. Pat. No. 4,537,201 with which the heart of a patient is stimulated by electrical stimulation pulses that are generated by a stimulation pulse generator and are supplied to the heart via an electrode arrangement. A contraction ensues, as a reaction of the heart to the stimulation, only when the stimulation energy exceeds a defined stimulation threshold deriving from the stimulation sensitivity of the heart tissue. In order to be able to adapt the stimulation energy to the variable stimulation sensitivity and thus to be able to keep the energy consumption low in the known heart pacemaker, the electrical potential in the heart tissue to be stimulated is acquired by a detector means and is interpreted after every stimulation to see whether a stimulation response, i.e. a reaction of the heart tissue as a consequence of the stimulation, is present. Every stimulation, however, causes polarization phenomena in the heart tissue having a multiply higher amplitude than the potential stimulation response to be detected. In order to enable an identification of the stimulation response in the curve of electrical potential measured by the detector means, the detector means of the known heart pacemaker contains a function generator that generates a signal curve after every stimulation pulse, which describes the polarization phenomena with a logarithmic time function. This signal curve is subtracted from the curve of the electrical potential measured in the heart tissue in a subtraction means and the difference signal obtained in this way is evaluated in an evaluation means for the presence or absence of a stimulation response.

In a further embodiment of the known heart pacemaker, the electrical potential curve acquired by the detector means in the tissue is linearized in an anti-logarithmic amplifier, whereby non-linear deviations from the linearized signal curve are subsequently detected in an evaluation means as a stimulation response of the heart.

In the two embodiments of the known heart pacemaker, the compensation of the polarization phenomena in the acquired curve of potential is based on the assumption that the curve of the polarization phenomena can be described with adequate precision by a defined mathematical equation. Patient-associated and other systemic and non-systemic deviations of the actual curve of the polarization phenomena from the assumed polarization curve, however, are not taken into consideration.

A so-called polarization compensation circuit is provided in another heart pacemaker disclosed in European Application 0 017 848, the polarization components being subtracted therein from the measured, electrical curve of potential of the heart. The difference signal obtained in such a way is evaluated for the presence of QRS waves and T waves. The manner by which the polarization component to be subtracted is obtained, however, is not disclosed in this European Application.

SUMMARY OF THE INVENTION

It is an object of the present invention to provide an apparatus for tissue stimulation wherein the polarization phenomena which occur as a result of this stimulation are compensated in signal evaluation circuitry, so that a reliable detection of the reaction of the tissue to the stimulation is possible.

The above object is achieved in a method and apparatus in accordance with the principles of the present invention wherein following a tissue stimulation, the chronological curve of the electrical tissue potential acquired by the detector means is intermediately stored in a first memory, the signal curve representing the polarization phenomena is stored in a second memory and, given the absence of a reaction of the tissue to the stimulation that is detected by the evaluation means, the intermediately stored, chronological curve of the electrical tissue potential is utilized for updating the signal curve in the second memory.

An important advantage of the invention is that a currently measured curve of the polarization phenomena is utilized instead of an assumed signal curve for the compensation of the polarization components contained in the acquired electrical curve of potential, so that the best possible compensation effect is achieved. The curve of the polarization phenomenon can be acquired in a simple way by stimulating the tissue with a stimulation energy lying below the stimulation threshold, so that the curve of the electrical potential in the tissue subsequently acquired by the detector means corresponds to the polarization phenomena produced by the stimulation attempt without these having a stimulation response of the tissue superimposed thereon. By regularly updating the signal curve in the first memory (which represents the polarization phenomena), an optimum compensation of the polarization components contained in the acquired curve of potential is achieved in the acquisition of the electrical curve of potential for the purpose of detecting a stimulation response.

Updating of the stored signal curve can be executed in the technologically simplest way by replacing the signal curve stored in the second memory each time with the intermediately stored, chronological curve of the electrical tissue potential.

Alternatively, a unit for forming the average value may be allocated to the first memory and to the second memory; the signal curve stored in the second memory and the chronological curve of the tissue potential intermediately stored in the first memory being used in this unit for forming the average value to form an average value signal for updating the signal curve stored in the second memory, this average value signal being stored in the second memory.

The evaluation of the difference signal can be executed in the simplest technological way wherein the evaluation means is a threshold detector for monitoring the difference signal for transgression of a prescribed threshold.

In order, when evaluating the difference signal, to also be able to take its signal width in consideration in addition to its amplitude, the evaluation means may be an integrator for integrating the difference signal with a following threshold detector for monitoring the integrated difference signal for transgressions of a prescribed threshold.

An evaluation independent of the respective reference potential (zero line) of the difference signal is achieved by preceding the threshold detector with a peak value memory for acquiring the peak-to-peak value of the difference signal, or of the integrated difference signal.

Although the stored signal curve utilized in the arrangement of the invention for the compensation of the polarization component in the acquired curve of electrical potential is constantly updated, it is not identical to the polarization component in the acquired curve of electrical potential. Since the polarization phenomena have a multiply higher amplitude than the potential stimulation response to be detected, even slight percentage differences between the polarization component of the currently acquired curve of potential and the stored signal curve can therefore make the evaluation of the difference signal more difficult. In a further embodiment of the invention, therefore, the polarization phenomena are reduced from the beginning in that the stimulation pulse generator generates biphase stimulation pulses.

DESCRIPTION OF THE PREFERRED EMBODIMENTS

Figure 1:
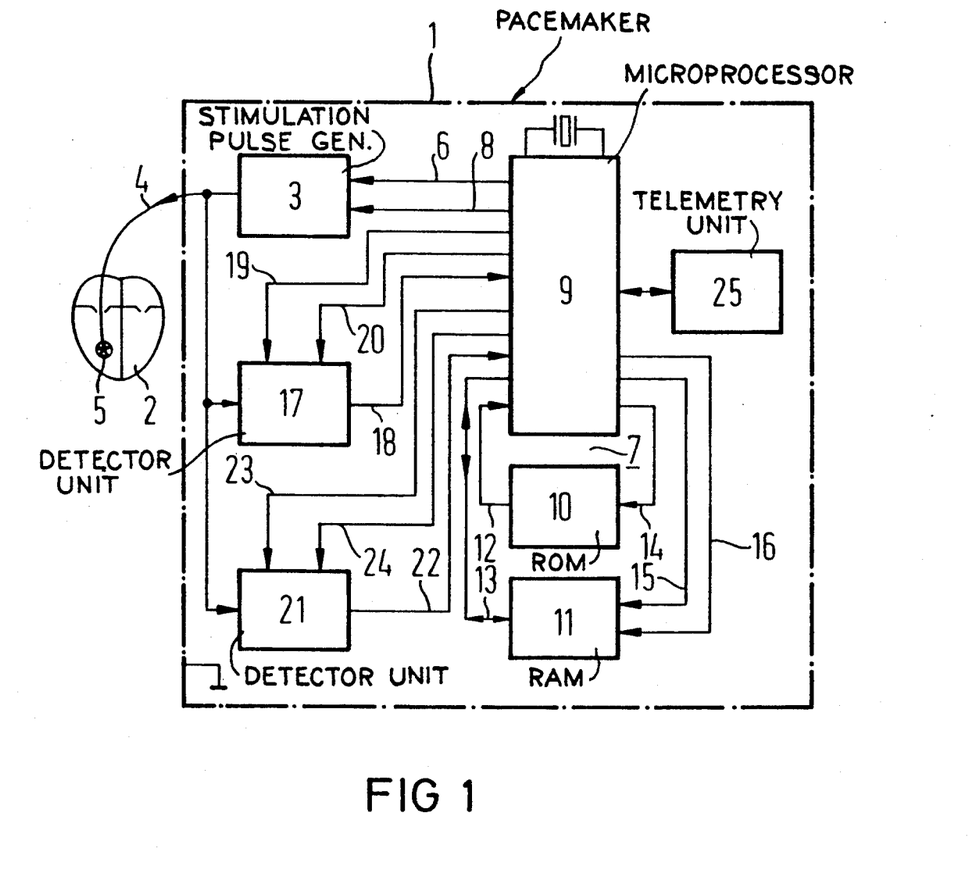
FIG. 1 is a schematic block diagram of an apparatus for tissue stimulation, in the form of a heart pacemaker, constructed in accordance with the principles of the present invention.

As an exemplary embodiment of the arrangement of the invention, FIG. 1 shows the block circuit diagram of a heart pacemaker 1 for tissue stimulation, in this case the stimulation of a heart 2. The heart pacemaker 1 contains a stimulation pulse generator 3 that has its output side connected via an electrode line 4 to an electrode 5 applied in the heart 2 for charging the heart 2 with stimulation pulses. The stimulation pulse generator 3 can be activated to deliver a stimulation pulse via a control line 6, which is connected to a corresponding output of a control unit 7. The duration of the respective stimulation pulse can also be set via the same line 6. For setting the amplitude of the stimulation pulses, the stimulation pulse generator 3 is connected via a further control line 8 to the control unit 7. In the illustrated exemplary embodiment, the control unit 7 is microprocessor 9 to which a read-only memory (ROM) 10 and a random access memory (RAM) 11 are assigned, these being connected to the microprocessor 9 via respective data lines 12 and 13, respective address lines 14 and 15, as well as via a write-read switching line 16 in the case of the random memory 11. A program that executes all functions of the heart pacemaker 1 via the microprocessor 9 is stored in the read-only memory 10.

In order to be able to acquire the reaction of the heart 2 given a stimulation, the heart pacemaker 1 contains a detector unit 17 which has an input side connected via the electrode line 4 to the electrode 5 for acquiring the electrical potential in the heart tissue. This arrangement is especially simple because only a single electrode 5 is required both for stimulating the heart 2 and for acquiring the reaction thereof (stimulation response). The problem arises, however, because the heart tissue is so highly polarized in the immediate region of the electrode 5, for every stimulation, that the polarization effects overlay the stimulation response of the heart 2 to the degree of making it unrecognizable. This problem and the inventive solution thereof shall be set forth in greater detail below with reference to FIG 2. The exemplary embodiment of the inventive arrangement of FIG. 1, for course, also allows the employment of a separate stimulation electrode and measuring electrode for respectively stimulating the tissue and for acquiring the stimulation response.

The curve of electrical potential in the heart tissue acquired by the detector unit 17 and evaluated for the presence or absence of a stimulation response is supplied via an output line 18 of the detector unit 17 to a corresponding input of the microprocessor 9 which, given the absence of a stimulation response, initiates an increase in the stimulation energy. If a response is detected, the detector unit 17 causes a decrease in the stimulation energy. The detector unit 17 is activated or inhibited by the microprocessor 9 via a control line 19, which may be composed of a plurality of individual lines for acquiring the curve of potential in the heart 2, and is set in terms of its sensitivity via a further control line 20. The structure of the detector unit 17 shall be set forth in greater detail below with reference to FIGS. 3 through 8.

For detecting natural heart activities, the heart pacemaker 1 contains a further detector unit 21 that also has its input side connected via the electrode line 4 to the electrode 5 and which is connected to the microprocessor 9 via an output line 22. The further detector unit 21 can be activated or disconnected and can be adjusted with respect to its sensitivity by the microprocessor 9 via control lines 23 and 24. The further detector means 21 serves the purpose of acquiring natural heart beats and of suppressing a stimulation of the heart 2 via the microprocessor 9 as long as natural heart activity is present; this function is known in the art and shall therefore not be set forth in greater detail below.

Finally, the heart pacemaker 1 contains a telemetry unit 25 connected to the microprocessor 9 for programming and for monitoring functions of the heart pacemaker 1 and of heart parameters acquired therewith on the basis of data exchange with an external programming and monitoring device (now shown).

Figure 2:
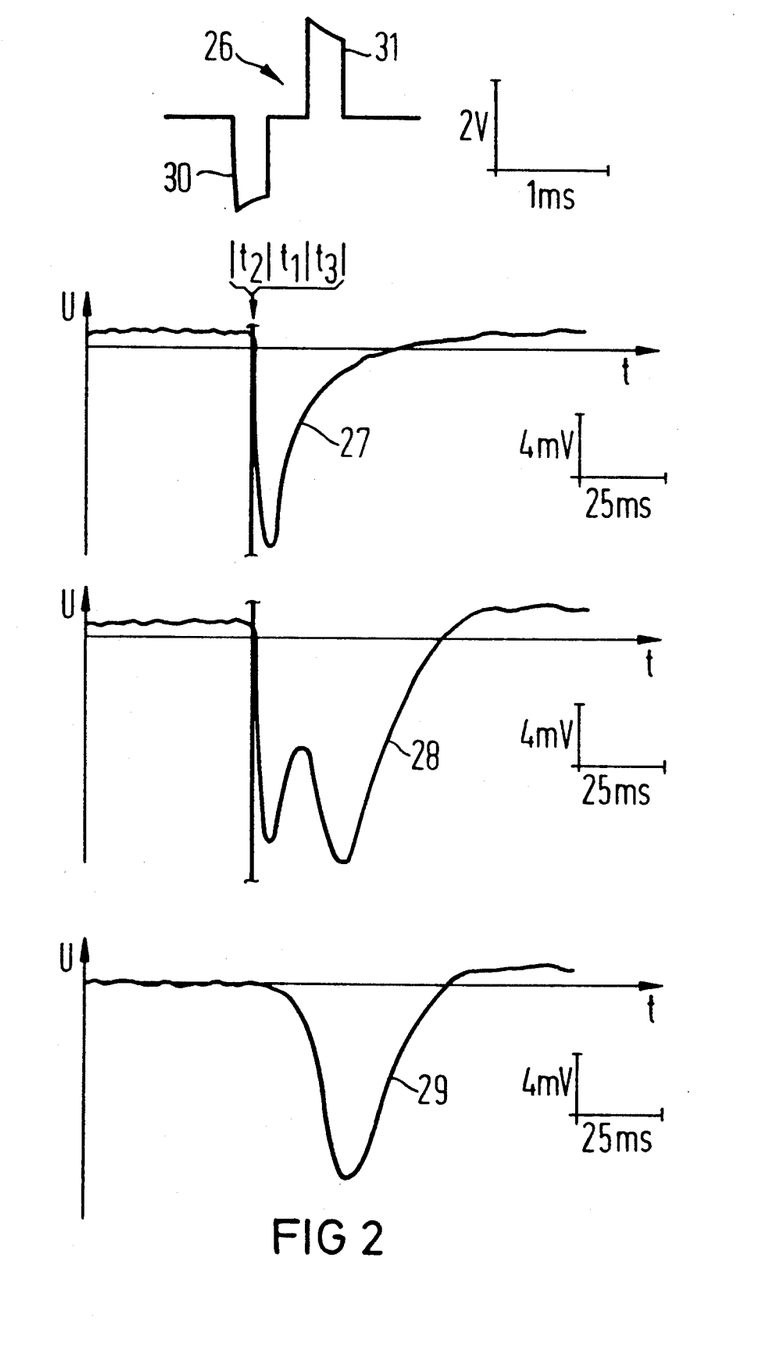
FIG. 2 shows a series of voltage/time diagrams representative of an unsuccessful stimulation attempt, and a difference signal formed therefrom.

In a time diagram from top to bottom, FIG. 2 shows a stimulation pulse 26 generated by the stimulation pulse generator 3 and supplied to the heart 2, a curve of the electrical potential 27 in the heart tissue produced by the stimulation pulse 26 given a stimulation energy lying below the stimulation threshold of the heart tissue to be stimulated, a curve of the electrical tissue potential 28 given a stimulation energy above the stimulation threshold and a difference signal 29 formed from the two potential curves 27 and 28. For clarity in illustrating the stimulation pulse 26, the amplitude thereof is shown compressed in comparison to the courses of the curves 27, 28, 29 and the chronological duration thereof is shown extended; due to the different scale of illustration, the stimulation pulse 26 appears as a vertical stroke in the respective curves of the tissue potential 27 and 28.

The illustrated stimulation pulse 26 is a biphase pulse composed of a negative sub-pulse 30 and of a positive sub-pulse 31 following thereupon after a pulse pause $t_1$. The pulse amplitudes and pulse durations $t_2$ and $t_3$ of the sub-pulses 30 and 31 are preferably the same. A variation of the stimulation energy is possible by varying the pulse amplitudes and/or the pulse durations $t_2$ and $t_3$. The advantage of the biphase stimulation pulse 26 over a monophase stimulation pulse (which may likewise employed within the framework of the invention) is in the relatively fast reduction of the polarization phenomena produced in the tissue via the stimulation as a result of the positive sub-pulse following the stimulation-triggering, negative sub-pulse 30, so that the acquisition of the reaction of the tissue to the stimulation (stimulation response) is facilitated in the case of a successful stimulation.

the curve of the electrical potential in the tissue referenced 27 represents a stimulation attempt with the stimulation pulse 26 and with a stimulation energy lying below the stimulation threshold, whereby the exponentially decaying curve section corresponds to the polarization phenomena produced in the tissue by the stimulation pulse 26. Due to the bipolarity of the stimulation pulse 26, the polarization phenomena are considerably reduced in comparison to a unipolar stimulation pulse.

The curve of the electrical tissue potential references 28 represents stimulation with a stimulation energy lying above the stimulation threshold of the heart tissue and also exhibits the exponentially decaying polarization phenomena on which, this time, the stimulation response of the heart 2 are superimposed. The stimulation response here is only visible on the basis of the polarization-reducing effect of the biphase stimulation pulse 26, and would be obscured by the polarization phenomena to the degree of being made unrecognizable in the case of a monophase stimulation. By forming the difference signal 28 from the curves 27 and 28, however, the stimulation response is filtered out of the curve of the tissue potential 28, even when the polarization phenomena have not been reduced by specific measures such as, for example, the employment of biphase stimulation pulses 26. Since, however, the stimulation phenomena form a signal component that is large in comparison to the stimulation response, relatively small percentage deviations in the curves 27 and 28 can also lead to a residual component remaining in the difference signal 29. This makes the detection of the stimulation response in the difference signal 29 more difficult. A reduction of the polarization phenomena from the very outset is therefore also preferable within the framework of the invention.

Figure 3:
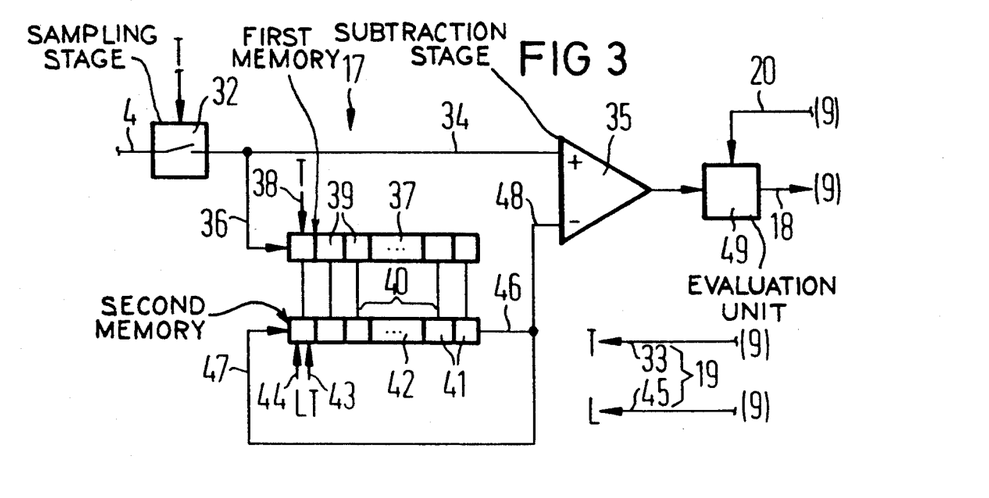
FIG. 3 is a schematic block diagram of a first embodiment of a detector unit for use in the apparatus of FIG. 1.

FIG. 3 shows a first exemplary embodiment of the detector unit 17 shown in FIG. 1 for forming and evaluating the difference signal 29 shown in FIG. 2. The input side of the detector unit 17 contains a sampling stage 32 connected via the electrode line 4 to the electrode 5, this sampling stage 32 being controllable by the microprocessor 9 with a sampling clock T via a clock control line 33. The output side of the sampling stage 32 is connected both to a first input 34 of a subtraction stage 35 and to a serial data input 36 of a first memory 37. The first memory 37 is connected to a clock control input 38 with the clock control line 33 and comprises a given plurality of memory locations 39 lying side-by-side, so that a sample supplied to the first memory 37 via the data input 37 is shifted from one memory location 39 to the next memory location 39 at every clock pulse T. The memory locations 39 are connected via parallel data output lines 40 to corresponding memory locations 41 of a second memory 42 that is likewise connected to a clock control input 43 with the clock control line 33. A further control input 44 of the second memory 42 can be charged with a data transfer signal L by the microprocessor 9 via a data transfer signal line 45 in order to copy the samples from the first memory 37 into the second memory 42 via the parallel data lines 40. Together, the two lines referenced 33 and 45 form the control line referenced 19 in FIG. 1. The second memory 42 is a circulating memory in that the last of the sequential memory locations 41 is connected to a serial data input 47 of the first memory location 41 via a serial data output 46. The serial data output 46 is also connected to a second input 48 of the subtraction stage 35. The subtraction stage 35 has an output side connected to an evaluation unit 49, which has an output connected to the microprocessor 9 via the output line 18. The sensitivity of the evaluation unit 49 can be set by the microprocessor 9 via the further control line 20.

It shall be assumed for explaining the functioning of the detector unit 17 shown in FIG. 3 that the samples of a signal curve which represents the polarization phenomena produced in the heart tissue by the stimulation are stored in the second memory 42. This, for example, can occur if the heart 2 is charged with a stimulation pulse 26 by the stimulation pulse generator 3, the stimulation energy of this pulse lying below the stimulation threshold of the heart tissue. Immediately after the stimulation, the microprocessor 9 generates the clock pulse T for a given chronological duration, the electrical potential in the heart tissue being sampled with this clock pulse T by the sampling stage 32 in a time window of 40-200 ms following the stimulation. The samples are entered in sequence into the memory locations 39 of the first memory 37 and are intermediately stored. Subsequently, the microprocessor 9 generates the data transfer signal L, whereupon the samples are copied from the memory locations 39 of the first memory 37 into the allocated memory locations 41 of the second memory 42. Samples of a signal curve are now present in the second memory 42 which correspond to the curve referenced 27 in FIG. 2, which represents the polarization phenomena produced in the tissue by the stimulation. There is also the possibility of loading the memory locations 41 of the second memory 42 with start values that are calculated in the microprocessor 9 according to an equation that approximately reproduces the course of the polarization phenomena, or that are derived from the read-only memory 10.

For monitoring the stimulation of the heart 2, the electrical potential after the output of a stimulation pulse 26 is samples in the heart tissue in the aforementioned time window by the sampling stage 32. The samples acquired in this way are successively supplied to the first input 34 of the subtraction stage 35 and are simultaneously intermediately stored in first memory 37. Synchronously therewith, the samples of the polarization phenomena stored in the second memory 42 are supplied to the second input 48 of the subtraction stage 35, and the same samples are again read in at the front into the second memory 42, so that they are not lost. If the stimulation energy was above the stimulation threshold of the heart tissue, the samples of the curve referenced 28 in FIG. 2 are present at the first input 34 of the subtraction stage 35, whereas the samples of the curve 27 are present at the second input. These two curves 27 and 28 are subtracted from one another in the subtraction stage 35, so that the evaluation unit 49 is supplied with the curve referenced 29 in FIG. 2, which reproduces the stimulation response. If the stimulation energy was below the stimulation threshold of the heart tissue, the samples of a curve of potential substantially corresponding to the curve 27 are supplied to the first input 34 of the subtraction stage 35. Since these samples differ only insignificantly from the samples stored in the second memory 42, a difference signal having at most a lower amplitude arises at the output of the subtraction stage 35, this being interpreted in the evaluation unit 49 as an absence of a stimulation response and being communicated to the microprocessor via the output line 18. In response thereto, the microprocessor 9 initiates a transfer—by generating the data transfer signal L—of the samples intermediately stored in the first memory 37 into the second memory 42. The curve of the polarization phenomena stored in the second memory 42 is updated in this way every time the evaluation unit 49 detects an absence of a reaction of the heart tissue to the stimulation.

Figure 4:
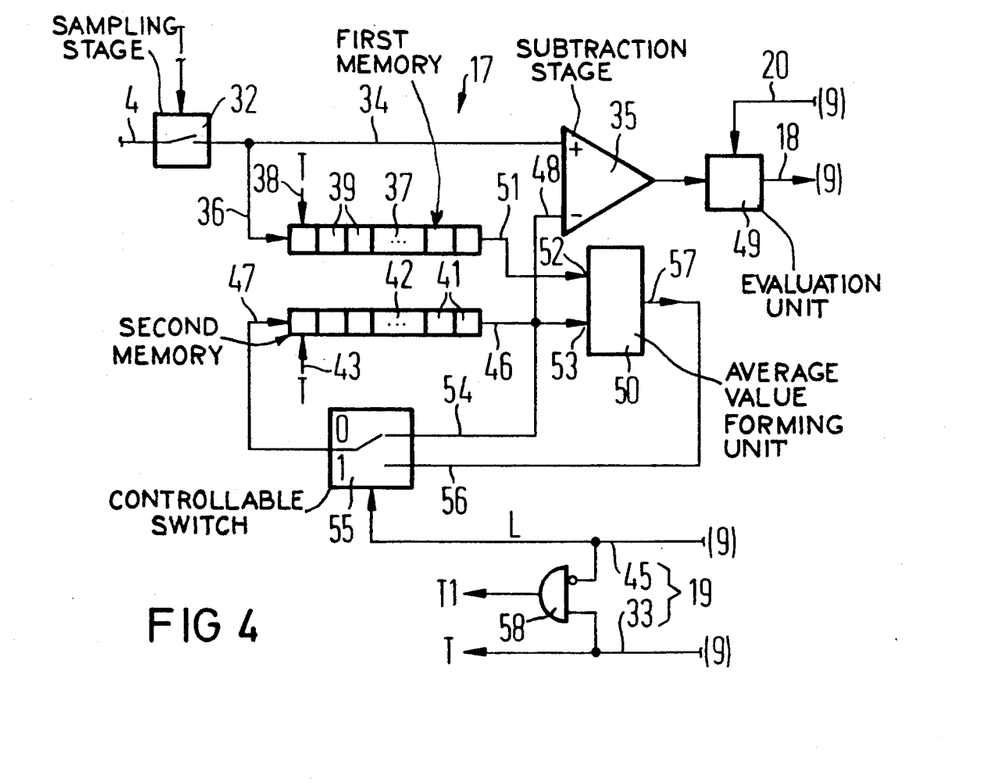
FIG. 4 is a schematic block diagram of a further embodiment of a detector unit for use in the apparatus shown in FIG. 1.

The exemplary embodiment of the detector unit 17 shown in FIG. 4 differs from the exemplary embodiment of FIG. 3 in that, for updating the signal curve deposited in the second memory 42, this signal curve is not simply replaced by the curve of the electrical tissue potential intermediately stored in the first memory 37; rather, both signal curves stored in the memories 37 and 42 are supplied to an average value forming unit 54 wherein the two signal curves are used to form an average value signal which is subsequently deposited in the second memory 42. The detector unit 17 shown in FIG. 4 thus comprises a sampling stage 32 controllable with a sampling clock T1 which has an input side connected via the electrode line 4 to the electrode 5 in the heart and has an output side connected to the first input 34 of a subtraction stage 35. The subtraction stage 35 is in turn followed by an evaluation unit 49 which is connected to the microprocessor 9 via the output line 18 and via the further control line 20. The sampling stage 32 also has its output side connected to a serial data input 36 of the first memory 37 which, differing from the exemplary embodiment of FIG. 3, has a serial data output 51 at the last of the memory locations 39 instead of parallel data output lines. The serial data output 51 is connected to a first input 52 of the average value forming unit 50. The second memory 42, which has an identical number of memory locations 41 as the first memory 37, has its serial data output 46 connected to both the second input 48 of the subtraction stage 35 and a second input 53 of the average value forming unit 50, and is additionally connected to a first switch contact 54 of a controllable switch 55 whose second switch contact 56 is connected to an output 57 of the average value forming unit 50. The switch 55 is controllable such with the signal L by the microprocessor 9 via the individual line 45 that the first switch contact 54 is connected to a serial data input 47 of the further memory 42 given L=0, and such that the second switch contact 56 is connected to the serial data input 47 given L=1. Differing from the clock pulses T for the two memories 37 and 42, the sampling clock pulses T1 for the sampling stage 32 are generated in a logic element 58 according to the logical operation T1=T·L.

When monitoring the stimulation of the heart 2, the switch 55 is in the switch position referenced "0", so that the values stored in the second memory 42 are supplied-simultaneously with the samples coming from the sampling stage 32 and supplied to the first input 34 of the subtraction stage 35—both to the second input 48 of the subtraction stage 35 and are also read back into the second memory 42 at the front via the switch 55. The signal curves supplied to the subtraction stage 35 via its inputs 34 and 48 are subtracted from one another in the same way already set forth with reference to FIG. 3, whereby the difference signal obtained in this way is checked in the evaluation means 49 for the presence or absence of a stimulation response. Given absence of a stimulation response, the switch 55 is driven into the switch position referenced "1" and the samples stored in the first memory 37 and in the second 42 are supplied in pairs to the average value forming unit 50, whereby the average values generated by the unit 50 are in turn supplied via the switch 55 to the second memory 52. The two memories 37 and 41 are thereby controlled by the clock pulses T, whereas the sampling clock pulses T1 for the sampling means 32 are inhibited as a result of L−1.

Figures 5, 6, 7:
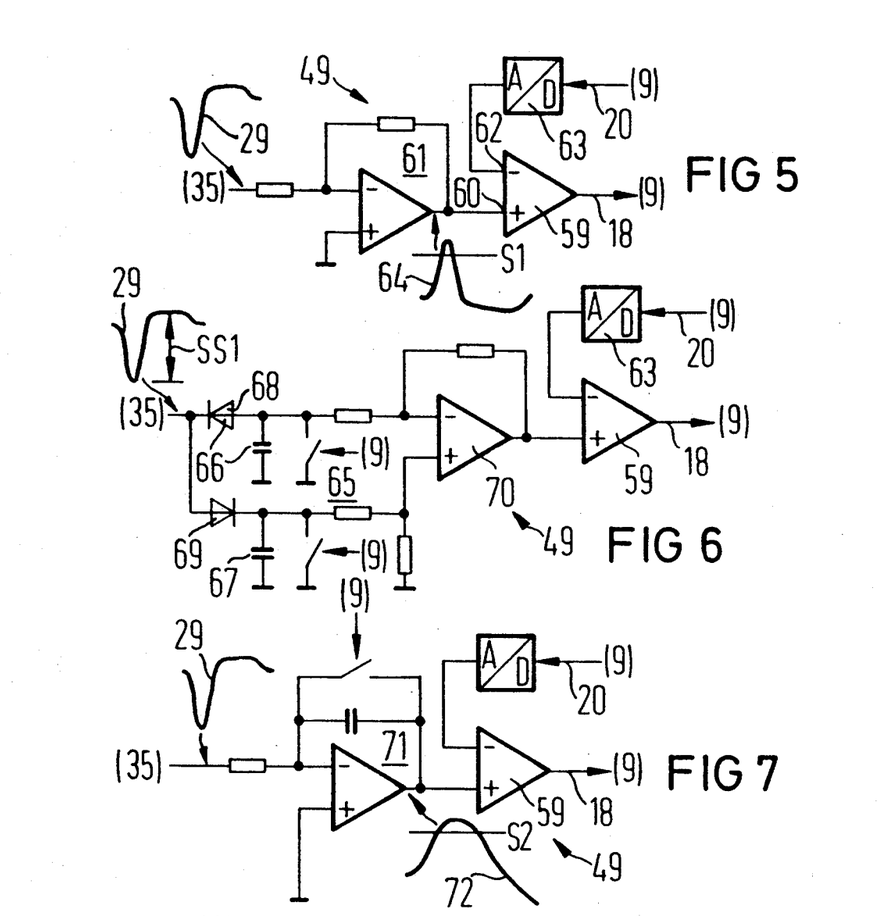
FIGS. 5, 6, 7 and 8 are respective schematic block diagrams for different embodiments of an evaluation unit for use in either of the embodiments of the detector unit shown in FIGS. 3 and 4.

The evaluation of the difference signal 29 formed by the subtraction stage 35 in the evaluation unit 49 shall be set forth below with reference to a number of exemplary embodiments of this evaluation unit 49. As set forth above, the difference signal at the output of the subtraction stage 35 given the presence of a stimulation response differs from the difference signal given the absence of a stimulation response on the basis of the significantly higher amplitude. In the simplest case, the evaluation unit 49 in accord with the exemplary embodiment of FIG. 5 is therefore a threshold comparator 59, whose non-inverting input 60 is directly connected to the output of the subtraction stages 35—or, as shown in FIG. 5, is connected thereto via an inverting amplifier 61—and whose inverting input 62 is supplied with a threshold signal S1 by the microprocessor 9 via a digital-to-analog converter 63. When the inverted difference signal 64 exceeds the threshold signal S1, the threshold comparator 59 generates an output signal that indicates the detection of a stimulation response to the microprocessor 9.

The exemplary embodiment of the evaluation unit 49 shown in FIG. 6 differs from the exemplary embodiment of FIG. 5 in that the inverting amplifier 61 is replaced by a peak value memory 65 that acquires the peak-to-peak value SS1 between the minimum and maximum of the difference signal 29 in the sampling time window that is employed. The peak value memory 65 is composed of two capacitors 66 and 67 which, via oppositely polarized diodes 68 and 69, are respectively charged with the positive or negative peak value of the difference signal 29. The two peak values are added in an adder 70 to form the peak-to-peak value SS1 that is monitored in the following threshold comparator 59 for the transgression of a threshold. The evaluation of the difference signal 29 is thereby independent of its respective reference potential (zero line). After every evaluation, the peak values stored in the capacitors 66 and 67 are erased by shorting the capacitors 66 and 67.

In the exemplary embodiment of FIG. 7, the threshold comparator 59 has its input side connected via an inverting integrator 71 to the output of the subtraction stage 35. Due to the integration of the difference signal 29 and the monitoring of the integration signal 72 for transgression of a threshold signal S2, not only the amplitude of the difference signal 29 but also the width of the difference signal 29 that is taken into consideration in the evaluation thereof. The integrator 71 is reset to an initial value after every evaluation.

Figure 8:
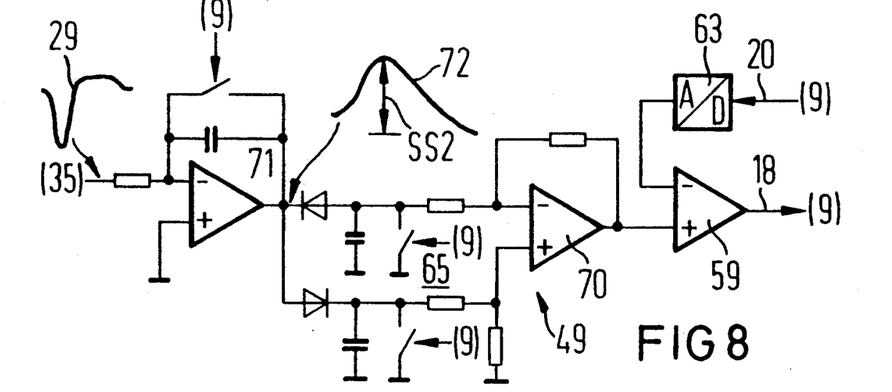

In the exemplary embodiment of the evaluation unit 49 shown in FIG. 8, the integrator 71, the peak value memory 65 and the threshold comparator 59 are connected in series to the output of the subtraction stage 35. In the evaluation of the difference signal 29, therefore, both the amplitude thereof and the width thereof are acquired, whereby the respective reference potential (zero line) of the difference signal 29 has no influence on the evaluation.

The precision of the monitoring of the stimulation can be further enhanced in that only those signal parts of the electrical potential acquired in the heart tissue which are typical of stimulated tissue reactions in terms of their frequency and steepness are forwarded for evaluation in the detector means 17. For this reason, the curve of potential acquired by the detector means 17 is frequency-limited by a band-pass filter—preferably before the sampling stage 32 because of the sampling theorem of Shannon. Because such a frequency limitation as well as a measuring amplification are generally standard in the acquisition of physiological signals, an illustration thereof has been foregone in the figures.

All possibilities of the signal evaluation shown and explained in conjunction with the figures can also be implemented by a program execution in the microprocessor 9 within the scope of the invention, in that the curve of potential acquired in the heart tissue is supplied to the microprocessor converted into digital values—either directly after the acquisition thereof or after a partial evaluation.

Although further modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for tissue stimulation comprising:
   pulse generator means for generating stimulation pulses;
   electrode means connected to said pulse generator means and adapted for in vivo connection to tissue for delivering said stimulation pulses to said tissue; and
   detector means for acquiring an electrical signal corresponding to electrical potential at said tissue, said electrical signal including signal components representing polarization phenomena produced by said tissue after a stimulation pulse, said detector means including a first memory in which said electrical signal is intermediately stored after each stimulation pulse, a second memory in which said signal components representing polarization phenomena are stored, subtraction means having inputs connected to said first and second memories for generating a difference signal from the contents in said first and second memories, means for evaluating said difference signal to identify the presence or absence of a reaction of said tissue to a stimulation pulse, and means for controlling entry into said first and second memories which, in the absence of a reaction of said tissue to a stimulation pulse, updates the contents of said second memory using the contents of said first memory.

2. An apparatus as claimed in claim 1 wherein said means for controlling entry is a means for replacing the contents of said second memory with the contents of said first memory.

3. An apparatus as claimed in claim 1 further comprising:
   average forming means connected to said first and second memories for forming an average of the respective contents of said first and second memories; and
   wherein said means for controlling entry is a means for replacing the contents of said second memory with said average formed by said average forming means in the absence of a reaction of said tissue to a stimulation pulse.

4. An apparatus as claimed in claim 1 wherein said means for evaluating includes a threshold detector which determines whether said difference signal exceeds a prescribed threshold.

5. An apparatus as claimed in claim 4 wherein said means for evaluating further includes a peak value memory means, preceding said threshold detector, for acquiring and storing a peak-to-peak value of said difference signal, and wherein said threshold detector determines whether said peak-to-peak value exceeds said prescribed threshold.

6. An apparatus as claimed in claim 1 wherein said means for evaluating includes an integrator means for integrating said difference signal followed by a threshold detector for determining whether the integrated difference signal exceeds a prescribed threshold.

7. An apparatus as claimed in claim 6 wherein said means for evaluating further includes a peak value memory means, preceding said threshold detector, for acquiring a peak-to-peak value of said integrated difference signal, and wherein said threshold detector determines whether said peak-to-peak value exceeds said prescribed threshold.

8. An apparatus as claimed in claim 1 wherein said pulse generator means is a means for generating biphasic stimulation pulses.

9. A method for stimulating tissue comprising:
   delivering a series of stimulation pulses in vivo to tissue;
   acquiring an electrical signal corresponding to electrical potential at said signal after a stimulation pulse, said electrical signal including signal components representing polarization phenomena produced by said tissue after a stimulation pulse;
   intermediately storing said electrical signal in a first memory after each stimulation pulse;
   storing said signal components representing polarization phenomena in a second memory;
   subtracting the contents of said first and second memories to obtain a difference signal after each stimulation pulse;
   evaluating said difference signal for the presence or absence of a reaction of said tissue to a stimulation pulse; and
   controlling entry into said first and second memories by, in the absence of a reaction of said tissue to a stimulation pulse, updating the contents of said second memory using the contents of said first memory.

10. A method as claimed in claim 9 wherein the step of controlling entry is further defined by replacing the contents of said second memory with the contents of said first memory in the absence of a reaction of said tissue to a stimulation pulse.

11. A method as claimed in claim 9 wherein the step of controlling entry is further defined by the steps of:
   forming an average of the respective contents of said first and second memories; and
   replacing the contents of said second memory with said average in the absence of a reaction of said tissue to a stimulation pulse.

* * * * *